US00PP37560P2

(12) United States Plant Patent
van Swieten

(10) Patent No.: US PP37,560 P2
(45) Date of Patent: Aug. 4, 2026

(54) ***PHALAENOPSIS* PLANT NAMED 'PHA844041'**

(50) Latin Name: *Phalaenopsis hybrida*
Varietal Denomination: PHA844041

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/316,675

(22) Filed: Sep. 2, 2025

(51) Int. Cl.
*A01H 5/02* (2018.01)
*A01H 5/12* (2018.01)
*A01H 6/62* (2018.01)

(52) U.S. Cl.
USPC ..... Plt./311
CPC ..... *A01H 6/62* (2018.05); *A01H 5/02* (2013.01); *A01H 5/12* (2013.01)

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP29,245 P3 * 4/2018 Van Swieten ..... A01H 6/62
Plt./311

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA844041', characterized by its upright and compact plant habit; moderately vigorous growth habit and slow to moderate growth rate; strong flowering stems; freely flowering habit with typically two inflorescences developing per plant, each inflorescence with numerous flowers; medium to broad white-colored flowers with greenish yellow and white labella; and good postproduction longevity.

2 Drawing Sheets

Figure 1:
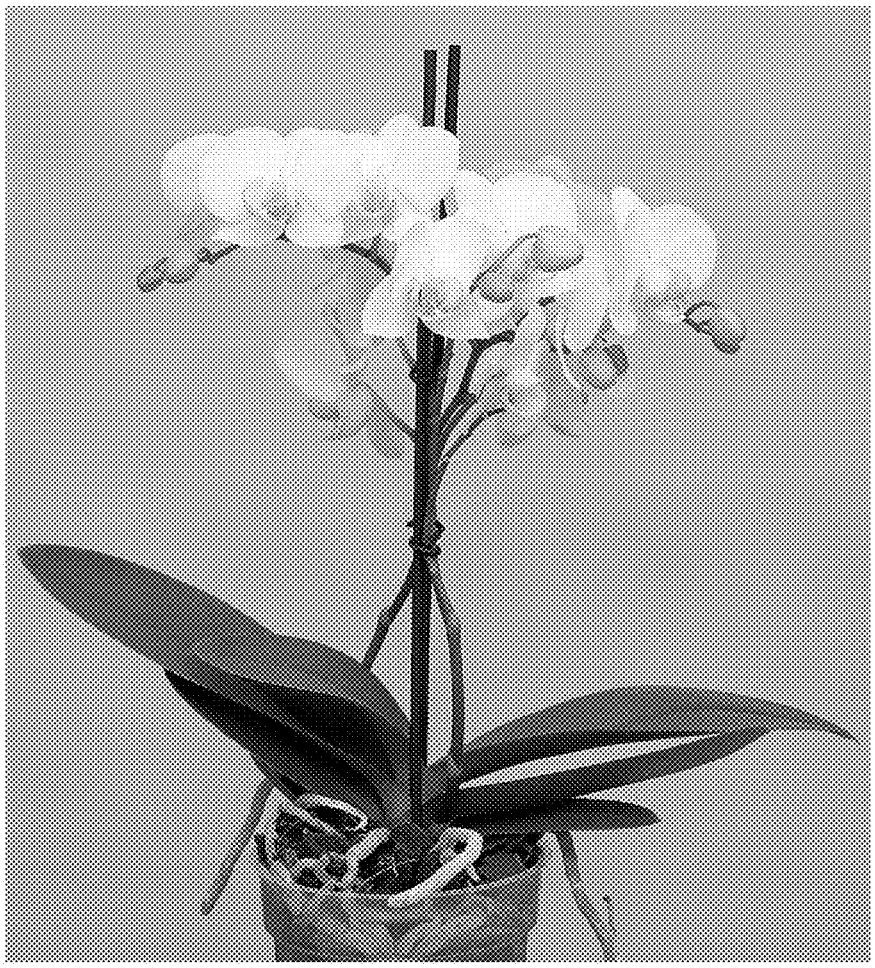

Botanical designation: *Phalaenopsis hybrida.*
Cultivar denomination: 'PHA844041'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Aug. 14, 2024, application number 2024/1892. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA844041'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique patterns and coloration.

The new *Phalaenopsis* plant originated from a cross-pollination in March, 2015 in Bleiswijk, The Netherlands of a proprietary breeding selection of *Phalaenopsis hybrida* identified as code number 09-043398-0001, not patented, as the female, or seed, parent with *Phalaenopsis hybrida* 'PHALGEPWAL', disclosed in U.S. Plant Pat. No. 30,990, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in December, 2017.

Asexual reproduction of the new *Phalaenopsis* plant by in vitro meristem propagation in a controlled environment in Bleiswijk, The Netherlands since December, 2017 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA844041'. These characteristics in combination distinguish 'PHA844041' as a new and distinct *Phalaenopsis* plant:

1. Upright and compact plant habit.
2. Moderately vigorous growth habit and slow to moderate growth rate.
3. Strong flowering stems.

4. Freely flowering habit with typically two inflorescences developing per plant, each inflorescence with numerous flowers.
5. Medium to broad white-colored flowers with greenish yellow and white labella.
6. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are semi-erect to horizontal in aspect whereas leaves of plants of the female parent selection are semi-erect in aspect.
2. The lateral lobes of the labella of plants of the new *Phalaenopsis* are more inwardly curved than the lateral lobes of the labella of plants of the female parent selection.

Plants of the new *Phalaenopsis* can be compared to plants of the male parent, 'PHALGEPWAL'. Plants of the new *Phalaenopsis* differ primarily from plants of 'PHALGEPWAL' in the following characteristics:

1. Flowers of plants of the new *Phalaenopsis* are broader than flowers of plants of 'PHALGEPWAL'.
2. The central lobes of the labella of plants of the new *Phalaenopsis* are narrowly deltoid in shape whereas the central lobes of the labella of plants of 'PHALGEPWAL' are trullate in shape.

Plants of the new *Phalaenopsis* can be compared to plants of *Phalaenopsis hybrida* 'PHA340530', disclosed in U.S. Plant Pat. No. 36,554. In side-by-side comparisons, plants of the new *Phalaenopsis* differ primarily from plants of 'PHA340530' in the following characteristics:

1. Flowers of plants of the new *Phalaenopsis* are broader than flowers of plants of 'PHA340530'.
2. Lateral sepals of plants of the new *Phalaenopsis* are white in color whereas lateral sepals of plants of 'PHA340530' are light yellowish green in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA844041' grown in a container.

Figure 2:
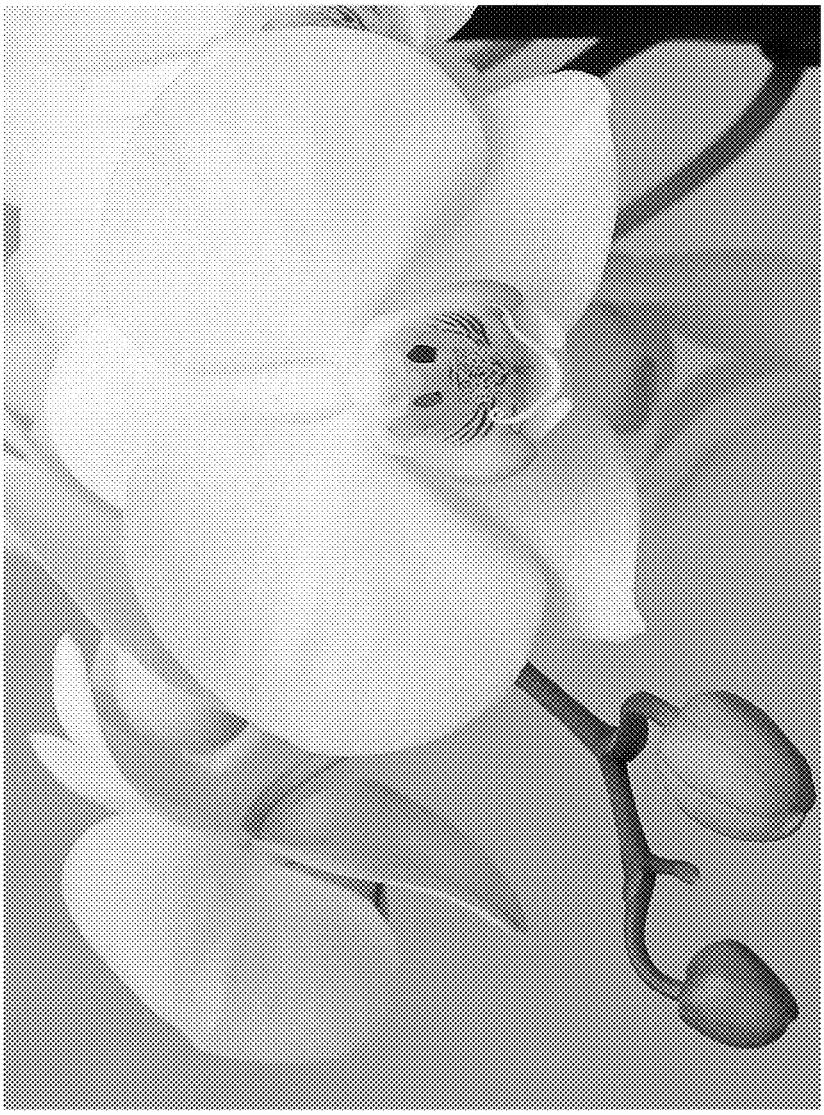

The photograph on the second sheet (FIG. 2) is a close-up view of typical flowers and flower buds of 'PHA844041'.

DETAILED BOTANICAL DESCRIPTION

The aforementioned photographs and following observations and measurements describe plants grown during the winter and early spring in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA844041'.

Parentage:

*Female, or seed, parent*.—Proprietary breeding selection of *Phalaenopsis hybrida* identified as code number 09-043398-0001, not patented.

*Male, or pollen, parent*.—*Phalaenopsis hybrida* 'PHALGEPWAL', disclosed in U.S. Plant Pat. No. 30,990.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright and compact plant habit with typically two inflorescences developing per plant, each inflorescence with numerous flowers; monopodial; moderately vigorous growth habit and slow to moderate growth rate.

*Plant height, substrate level to top of foliar plane*.—About 11.2 cm.

*Plant height, substrate level to top of floral plane*.—About 27.5 cm.

*Plant diameter or spread*.—About 29.6 cm.

Leaf description:

*Arrangement and quantity*.—Distichous, simple; sessile; about four to six fully-developed leaves per plant.

*Length*.—About 17.9 cm.

*Width*.—About 6.4 cm.

*Aspect*.—Semi-erect to horizontal.

*Shape*.—Narrowly obovate to oblanceolate; slightly carinate.

*Apex*.—Unequal acute.

*Base*.—Sheathing. Sheath length: About 1.7 cm. Sheath width: About 1.2 cm. Sheath color: Close to 143C and 144B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B; narrow marginal edges, close to 144B. Developing leaves, lower surface: Close to 146B; narrow marginal edges, close to 144B. Fully expanded leaves, upper surface: Close to NN137A; narrow marginal edges, close to 144A; venation, close to 147A. Fully expanded leaves, lower surface: Close to 146A; narrow marginal edges, close to 144A; venation, close to 146B.

Inflorescence description:

*Appearance and flowering habit*.—Showy zygomorphic flowers arranged on axillary simple or branched racemes; typically two inflorescences develop per plant; each inflorescence with about 16 flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about eleven weeks on the plant; flowers not persistent.

*Inflorescence length* (*lowermost flower to inflorescence apex*).—About 20.3 cm.

*Inflorescence width*.—About 13.5 cm.

*Flower buds*.—Height: About 1.6 cm. Diameter: About 1.3 cm by 1.6 cm. Shape: Broadly ovate. Color: Close to a blend of 145B and 150B.

*Flower size*.—About 6 cm (vertical) by 6.7 cm (horizontal).

*Flower depth*.—About 2.8 cm.

*Petals, quantity and arrangement*.—Three, two lateral petals and one center petal transformed into a labellum.

*Lateral petals*.—Length: About 3.2 cm. Width: About 3.7 cm. Shape: Broadly reniform. Apex: Obtuse. Margin: Entire; not undulate. Texture and luster, upper and lower surfaces: Smooth, glabrous; moderately velvety; matte. Color: When opening, upper surface: Close to NN155B. When opening, lower surface: Close to 155C; towards the margins, close to NN155B. Fully opened, upper and lower surfaces: Close to NN155D; color does not change with subsequent development.

*Labella*.—Appearance: Three-parted with two lateral lobes and a central lobe; overall shape, broadly cordate. Length, lateral lobes: About 1.8 cm. Width, lateral lobes: About 1.4 cm. Length, central lobe: About 1.6 cm. Width, central lobe: About 4 mm to 18 mm. Length, cirrhose tips: About 1 cm. Shape, lateral lobes: Obovate. Shape, central lobe: Narrowly deltoid with a slightly elongated apex. Apex, lateral lobes: Obtuse. Apex, central lobe: Narrowly acute to shallow retuse with two cirrhose apices, curled and pointing upwards and backwards (not always present). Margins, lateral and central lobes: Entire. Texture and luster, lateral and central lobes, upper and lower surfaces: Smooth, glabrous; velvety; matte. Callosities: Located at the base of the labellum and attachment point of the lateral petals; about 4 mm in length, about 4 mm in width and about 4 mm in height. Color: When opening, upper surface: Lateral lobes: Close to NN155D; lower margins, close to 7A; at the base, axial stripes, close to 181A. Central lobe: Close to NN155A; towards the apex, close to NN155C; narrow apical edges, close to N170A; towards the base, close to 5B and at the base, close to 157C to 157D with radial stripes, close to 172B; cirrhose apices, close to NN155C. Callosities: Close to 4D; at the apex, close to 12B with fine dots, close to 178C. When opening, lower surface: Lateral lobes: Close to NN155C; lower margins, close to 12A; at the base, close to 156D. Central lobe: Close to 155C; narrow apical edges, close to N170A; towards the base, close to 2B and at the base, close to 157C to 157D; midvein, close to 145B to 145C; cirrhose apices, close to 155C. Fully opened, upper surface: Lateral lobes: Close to NN155D; lower margins, close to 12A; at the base, axial stripes, close to 181B and 181C. Central lobe: Close to NN155C; towards the apex, close to NN155D; narrow apical edges, close to N170A; towards the base, close to 12B and at the base, close to 157C to 157D with radial stripes, close to 172B; cirrhose apices, close to NN155D. Callosities: Close to 8C; at the apex, close to 13B and 13C with fine dots, close to 178C. Fully opened, lower surface: Lateral lobes: Close to NN155D; lower margins, close to 13B; at the base, close to 156D. Central lobe: Close to NN155A; narrow apical edges, close to N170A; towards the base, close to 2A and at the base, close to 157D; midvein, close to 145C to 145D; cirrhose apices, close to NN155A.

*Sepals*.—Quantity and arrangement: Three, one upper dorsal sepal and two lower lateral sepals. Length, dorsal sepal: About 3.3 cm. Width, dorsal sepal: About 2.1 cm. Length, lateral sepals: About 3.4 cm. Width, lateral sepals: About 2.1 cm. Shape, dorsal sepal: Elliptic. Shape, lateral sepals: Ovate. Apex, dorsal sepal: Obtuse to shallow retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 157D. When opening, lower surface: Close to 145C; towards the apex and margins, close to 145D; towards the base, close to a blend of 145D and 150D. Fully opened, upper surface: Close to NN155D. Fully opened, lower surface: Close to NN155C; towards the apex, slightly tinged with close to 186D. Color, lateral sepals: When opening, upper surface: Close to 157B; lower half, close to a blend of 145D and 150D; at the base, fine dots, close to 152D. When opening, lower surface: Close to 145C; midvein, close to 145A to 145B. Fully opened, upper surface: Close to NN155D; lower half, close to NN155B; at the base, fine dots, close to 186B. Fully opened, lower surface: Close to NN155C; lower half, close to 155C; midvein, slightly tinged with close to 186C.

*Peduncles*.—Length: About 30.1 cm. Diameter: About 4.5 mm. Strength: Strong. Aspect: Upright to outwardly arching. Texture and luster: Smooth, glabrous; matte. Color: Close to 137B with dense fine dots and marbling, close to 151B and 151C.

*Pedicels*.—Length: About 3.3 cm. Diameter: About 2.5 mm. Strength: Moderately strong. Aspect: About 50° from peduncle axis. Texture and luster: Smooth, glabrous; matte. Color: Close to 144B; distal end, close to 145D; proximal end, close to 146A.

*Reproductive organs*.—Androecium: Column length: About 7 mm. Column width: About 5 mm. Column color: Close to NN155C. Pollinia quantity: Two. Pollinia diameter (per two pollinia): About 2 mm. Pollinia color: Close to 23A. Gynoecium: Stigma length: About 3.5 mm. Stigma width: About 4 mm. Stigma shape: Reniform. Stigma color: Close to 155C. Ovary length: About 1.7 cm. Ovary diameter: About 1 mm. Ovary color: Close to 150C. Seeds and fruits: To date, seed and fruit development have not been observed on plants of the new *Phalaenopsis*.

Pathogen & pest resistance:

To date, plants of the new *Phalaenopsis* have not been shown to resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA844041' as herein illustrated and described.

* * * * *